United States Patent
Boese et al.

(10) Patent No.: US 7,760,926 B2
(45) Date of Patent: Jul. 20, 2010

(54) METHOD AND DEVICE FOR MARKING THREE-DIMENSIONAL STRUCTURES ON TWO-DIMENSIONAL PROJECTION IMAGES

(75) Inventors: Jan Boese, Eckental (DE); Andreas Meyer, Möhrendorf (DE); Marcus Pfister, Bubenreuth (DE); Norbert Rahn, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 1070 days.

(21) Appl. No.: 11/453,623

(22) Filed: Jun. 15, 2006

(65) Prior Publication Data
US 2006/0285738 A1 Dec. 21, 2006

(30) Foreign Application Priority Data
Jun. 15, 2005 (DE) .................. 10 2005 027 678

(51) Int. Cl.
*G06K 9/00* (2006.01)
(52) U.S. Cl. .................. 382/131; 382/128; 382/132; 382/154; 356/12
(58) Field of Classification Search ......... 382/128–134, 382/154; 356/12; 348/419–427
See application file for complete search history.

(56) References Cited

U.S. PATENT DOCUMENTS

| 6,493,575 | B1 | 12/2002 | Kesten et al. | |
| 6,501,848 | B1* | 12/2002 | Carroll et al. | 382/128 |
| 7,127,081 | B1* | 10/2006 | Erdem | 382/103 |
| 2004/0133379 | A1* | 7/2004 | Kobayashi et al. | 702/127 |
| 2004/0249594 | A1* | 12/2004 | Satoh et al. | 702/104 |
| 2005/0033160 | A1 | 2/2005 | Yamagata et al. | |

FOREIGN PATENT DOCUMENTS

| DE | 199 62 666 A1 | 7/2001 |
| DE | 100 57 023 A1 | 6/2002 |

* cited by examiner

*Primary Examiner*—Samir A. Ahmed
*Assistant Examiner*—Ali Bayat

(57) ABSTRACT

The invention relates to a method and a device for marking three-dimensional structures on two-dimensional projection images of an object, with which a position marker is determined on two projection images of the object recorded from different projection directions, from which the position of the position marker in the three-dimensional space is calculated so that further, subsequently recorded projection images can be displayed superimposed by the position marker.

19 Claims, 2 Drawing Sheets

METHOD AND DEVICE FOR MARKING THREE-DIMENSIONAL STRUCTURES ON TWO-DIMENSIONAL PROJECTION IMAGES

CROSS REFERENCE TO RELATED APPLICATIONS

This application claims priority of German application No. 10 2005 027 678.4 filed Jun. 15, 2005, which is incorporated by reference herein in its entirety.

FIELD OF THE INVENTION

The invention relates to a method and a device for marking three-dimensional projection images on two-dimensional projection images, with the projection images being recorded with an image recording system, which allows projection images to be recorded from different projection directions. In particular, the invention can be used with interventional x-ray devices.

BACKGROUND OF THE INVENTION

Numerous medical interventions are nowadays controlled by means of intraoperatively obtained x-ray images. By way of example, x-ray images, so-called fluoroscopic images, are often recorded in real-time in order to navigate the instruments during neurosurgical or other minimally invasive interventions. The x-ray devices used for this purpose are mostly equipped with an image recording system, which allows projection images to be recorded from the most varied of projection directions so as to be able to view the examination area from the line of vision suitable in each instance. The so-called C-arm systems are popular here, such as for instance the device AXIOM Artis by Siemens AG, with which x-ray tubes and x-ray detectors are fixed to the ends of a C-arm which can be moved freely about the patient. Furthermore, the patient support can also be adjusted.

However, the two-dimensional (2D) projection images obtained in this way do not contain depth information and thus do not display any spatial details. A three-dimensional (3D) display of the changes in the image content during the entire diagnostic or surgical intervention would be ideal for the surgeon. However, with present-day imaging modalities, it is not possible to obtain 3D images in real-time.

In the prior art, the missing spatial information in the intraoperatively obtained projection images is hereby sometimes compensated for in that preoperatively recorded three-dimensional images (3D images) are view together with the two-dimensional projection images (2D images). This combination of current 2D images and spatially triggered 3D images enables the doctor to orientate him/herself in the volume during the intervention, however, no structures are visible in the preoperatively recorded 3D images. The structures are only inserted into the examination area during the intervention. Furthermore, it is difficult to spatially correspond (register) the preoperative 3D images to the intraoperative projection images.

SUMMARY OF THE INVENTION

The object of the invention is thus to develop a method and a device to facilitate the examiner or surgeon with orientation in the examined object particularly during an image-controlled intervention.

The invention achieves this object with the features of the claims. Preferred embodiments of the invention are specified in the dependent claims.

The method according to the invention is characterized by the following steps: (a) recording two projection images of the object from different projection directions; (b) determining a position marker on the two projection images; (c) calculating the position of the position marker in the three-dimensional space; (d) recording a further projection image with the image recording system and calculating the theoretical position of the position marker on the projection image; and (e) displaying the projection image recorded in step (d) superimposed by the position marker.

The invention thus aims to support the examiner or surgeon by means of suitable graphic collimations, e.g. during a diagnostic or surgical intervention. In fact, the examiner can select a structure on the two projection images recorded in step (a) and mark its position with a position marker. The structure can be a vessel made visible in the short term for instance by a contrast means, which the examiner would also like to identify on the subsequently recorded projection images without having to re-inject contrast means. The examiner can thus determine the position marker in the form of a line on the two projection images following the vessel for instance. The coordinates of the position marker in the three-dimensional space are herewith clearly determined. In this way, the position of the position marker on all further recorded projection images can be calculated and the projection images are displayed superimposed by the position marker.

This assumes that the image recording system is calibrated, which means that with a C-arm system for instance, the change in the field of vision resulting from a change in the angulation of the C-arm or from a displacement of the patient support is known or can be calculated. If this is not the case, the further projection images recorded in step (d) must first be spatially registered with the projection images recorded in step (a). The calibration or registration allow the theoretical position of any three-dimensional structure in the space on a projection image recorded using any settings (angulation, displacement of the patient support etc.) to be calculated. In other words, when the position of a structure in the examination area is known, it is possible to calculate where this structure would be imaged on a projection image recorded from any projection direction. Projection images recorded subsequently can thus be superimposed with the position marker.

As mentioned above, the image recording system is preferably a part of an x-ray system and in particular a C-arm system. So-called biplan systems comprising two x-ray detectors are particularly preferable so that the two projection images can be recorded almost simultaneously and thus automatically in almost the same movement phase of the object.

The examined object is preferably a part of the human or animal body, which is subjected to a diagnostic or surgical intervention for instance during the application of the method according to the invention.

The position marker is made up of points, lines, surfaces or other geometric figures and marks the position of a structure within the examined object. The type and the position of the position marker are preferably determined by the examiner. By way of example, points can be selected on the two projection images with the aid of a mouse, or the examiner can span lines, triangles, ellipses or other geometric figures which outline a structure of interest to him/her. In the case of an electrophysiological intervention, a vascular process, a bile duct containing a contrast means or the contour of a heart chamber for instance, the position marker marks the position of an implemented or planned ablation. The marking of structures which are only visible in the short term is particularly advantageous, such as for instance contrasted blood vessels or those first inserted during the intervention, such as the ablation sites.

Alternatively, the position marker can also be automatically fully or partially determined by image segmentation with the aid of a computer for instance.

If the examined object such as for instance the heart or the coronary arteries, is subjected to respiratory movement and/or heart beat movements, the recording of the projection images is preferably controlled by respiratory triggering and/or ECG triggering.

The invention is also aimed at a device which is preferably suited to implementing the above-described method and further comprises (a) a first data storage means for storing two projection images of the object from different projection directions; (b) a means for determining a position marker on the two projection images; (c) a computer for calculating the position of the position marker in the three-dimensional space, as well as for calculating the theoretical position of the position marker on other projection images of the object recorded from other projection angles, and (d) a screen for displaying further projection images of the object superimposed by the position marker.

The means for determining the position marker is preferably a mouse or another cursor control means, with which a user can select points on the two projection images, or a computer which fully or partially automatically determines a position marker.

The image recording system is preferably a part of an x-ray device and comprises an x-ray tube and an x-ray detector which can be moved about the object, in particular a patient.

BRIEF DESCRIPTION OF THE DRAWINGS

Preferred embodiments of the invention are described from now on with reference to the appended drawings, in which:

FIG. 1A, 1B show two projection images of a vessel tree with a position marker drawn-in;

DETAILED DESCRIPTION OF THE INVENTION

Figure 1A:
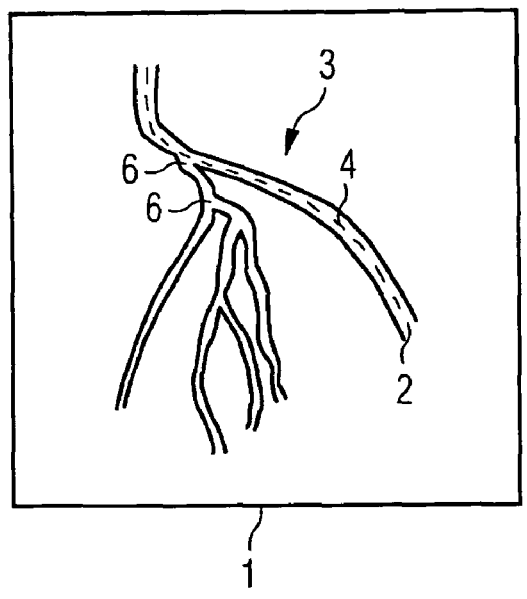
Figure 1B:
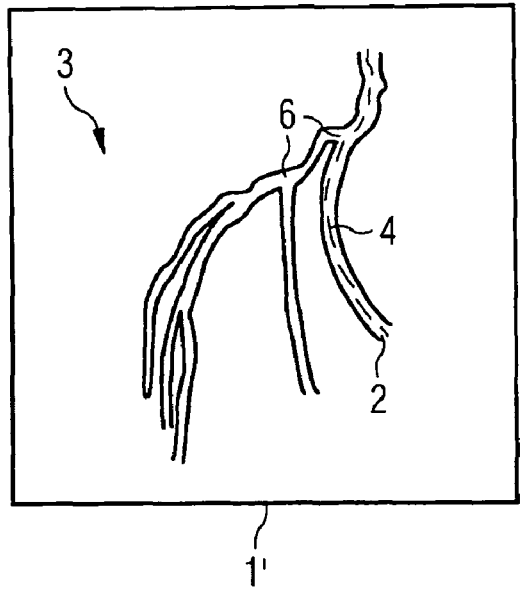

FIG. 1 shows a schematic representation of two projection images 1, 1' of a vessel tree 3 recorded from different projection angles. These images were recorded for instance during administration of intra-arterial contrast means by means of a biplane system, so that the vessels can be recognized with a high level of contrast.

In particular, the vessel tree 3 features a main artery 2 and two vessel branches 6. If the examiner or surgeon would also like to make the main artery 2 visible on subsequent projection images, in particular fluoroscopic images, he can trace the path of the main artery 2 on the two projection images 1, 1' by means of a position marker 4. In this case, the position marker 4 is a (dashed) line. With other vessels, e.g. with the outlet from the left atrium of the heart in the direction of the lungs, an ellipse can also be selected as a position marker.

The position marker 4 must be marked on at least two projection images. Since the marker is generally a relatively simple geometric figure, its relative position in the space is thus determined. The position of the marker can optionally also be marked or controlled on further projection images. Furthermore, the position marker can also contain further elements, e.g. points (not shown) arranged on the vessel branches 6.

Figure 3:
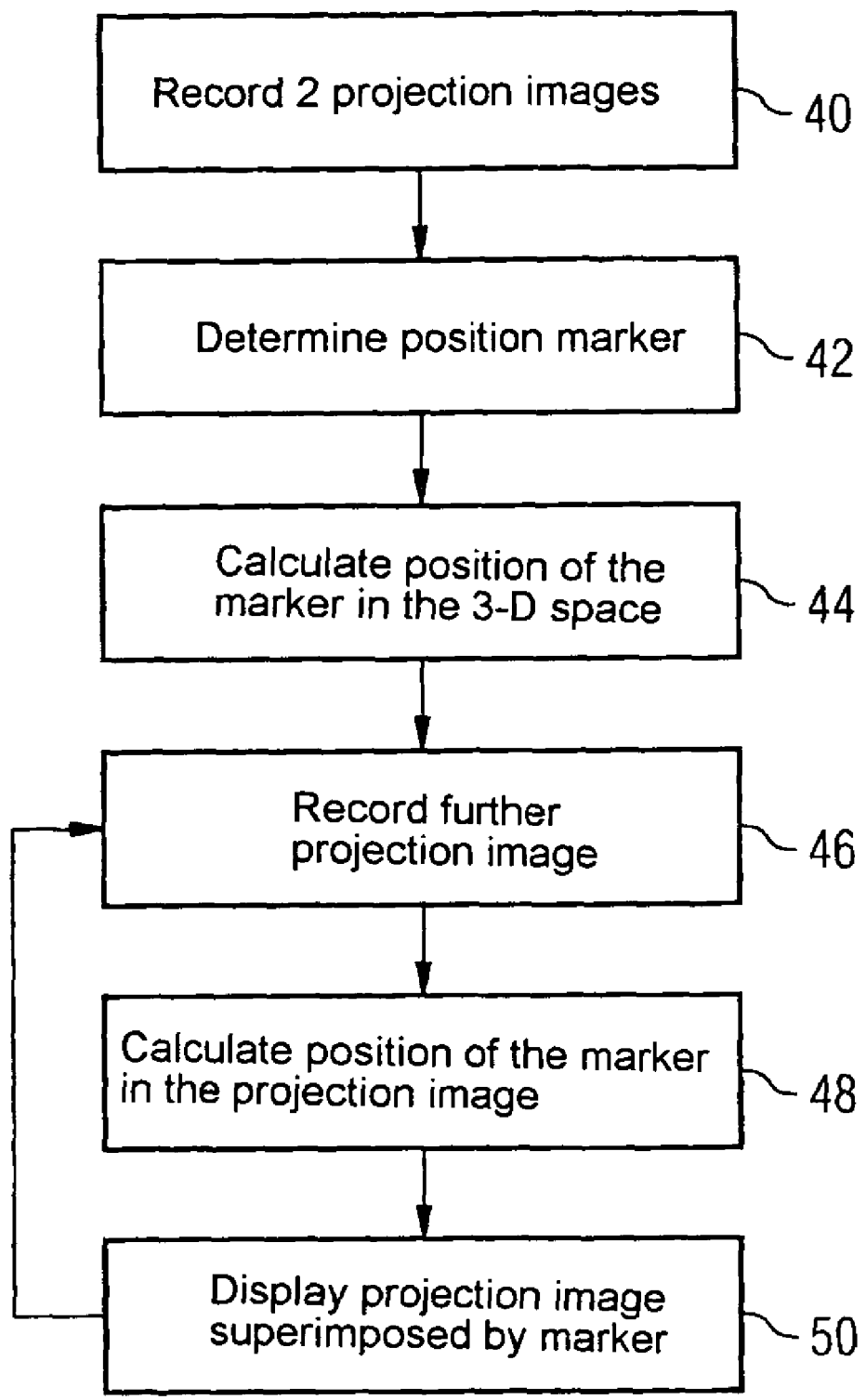
FIG. 3 shows a flow diagram of an embodiment of the method according to the invention.

FIG. 1 illustrates the step "determine position marker" indicated with 42 in the flow diagram of FIG. 3. The position of the position marker in the three-dimensional space is subsequently calculated in step 44. Further projection images can now be recorded if necessary from other projection directions (Step 46) and the theoretical position of the position marker is calculated on these projection images (Step 48). This allows the position marker to be shown in the further projection images (step 50). This enables the examiner or surgeon to retain the path of the arteries 2 on all further projection images, even if these were recorded with other angulations or displacements of the patient support. With moving objects, a respiratory triggering or ECG triggering of the projection images is required for this purpose, so that the projection images are recorded in each instance in the same movement phase.

Figure 2:
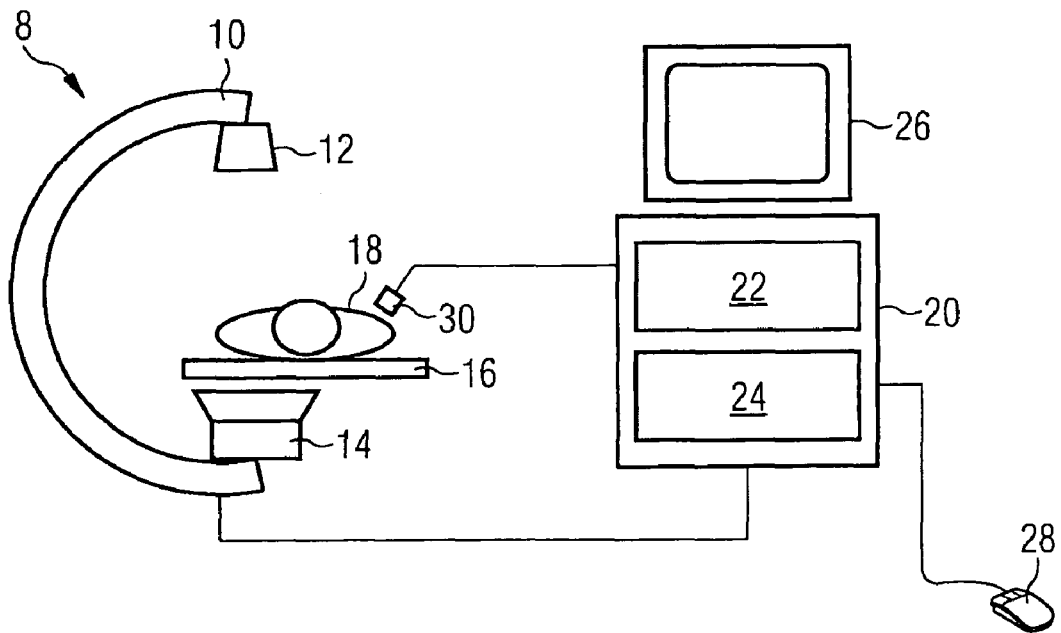
FIG. 2 shows a schematic representation of an embodiment of the device according to the invention.

An exemplary embodiment of a device suited to implementing the above-described method is displayed in FIG. 2. This features an image recording system 8 with a C-arm 10, to the end of which an x-ray tube 12 and an x-ray detector 14 are fixed in each instance. The C-arm can be moved freely about a patient support 16, on which a patient 18 is positioned. X-ray images of the patient can be acquired from any projection directions.

These are transmitted to the data storage means 22 of a control and image processing computer 20. The computer 20 further contains a computing module 24, with which the position of the position marker in the three-dimensional space, as well as its position on further projection images can be calculated. To this end, further data for calibrating the image recording system is stored in the data storage means 22.

An ECG probe 30 is fixed to the patient 18, which records an electrocardiogram. This is transmitted to the control and image processing computer 20 and is used if necessary to trigger the recording of the projection images at a specific time in the heart cycle. This ensures that all projection images are recorded in the same movement phase of the heart.

A screen 26 for displaying the projection images and a mouse 28 for selecting points, lines etc on the projection images are further connected to the control and image processing computer 20. A user can thus determine a position marker on the projection images with the aid of the mouse 28. Alternatively, the means of determining the position marker may also be for instance another cursor movement means such as a trackball, a touch screen or a computing module, which determines the position marker by means of image segmentation for instance.

The invention claimed is:

1. A method for marking a three-dimensional structure on a two-dimensional projection image of an object recorded with an image recording system, comprising:
   recording two two-dimensional projection images of the object from two different projection directions;
   determining a position marker on each of the two two-dimensional projection images;
   calculating coordinates of the position marker in a three-dimensional space based on each of the two two-dimensional projection images;
   recording a further two-dimensional projection image from a further projection direction;
   using the calculated coordinates of the position marker in the three-dimensional space, calculating theoretical coordinates for the position marker in the further recorded two-dimensional projection image; and applying the calculated theoretical coordinates to display the further recorded two-dimensional projection image with the calculated theoretical position of the position marker superimposed thereon;

generating an image with the position marker superimposed on the further recorded two-dimensional projection image in accord with the calculated theoretical coordinates for the position marker; and displaying the further recorded two-dimensional projection image with the position marker superimposed thereon.

2. The method as claimed in claim 1, wherein steps of recording a further two-dimensional projection image from a further projection direction, calculating a theoretical position of the position marker on the further recorded two-dimensional projection image in the three-dimensional space, and displaying the further recorded two-dimensional projection image superimposed by the calculated theoretical position of the position marker are repeated.

3. The method as claimed in claim 1, wherein the position marker is a geometric figure which marks a position of a structure within the object.

4. The method as claimed in claim 3, wherein the position marker is selected from the group consisting of: points, lines, and surfaces.

5. The method as claimed in claim 1, wherein the position marker is determined by a medical examiner.

6. The method as claimed in claim 1, wherein the image recording system is a part of a medical x-ray system.

7. The method as claimed in claim 6, wherein the image recording system is a C-arm system.

8. The method as claimed in claim 7, wherein the further recorded two-dimensional projection image differs from the two two-dimensional projection images by the C-arm angulation.

9. The method as claimed in claim 1, wherein the further recorded two-dimensional projection image differs from the two two-dimensional projection images by a table displacement.

10. The method as claimed in claim 9, wherein the table is a part of the image recording system on which the object is positioned.

11. The method as claimed in claim 1, wherein the object is a part of a human or animal body and the step of determining a position marker on each of the two two-dimensional projection images is performed by marking a structure which is only visible in the short term with use of a contrast means.

12. The method as claimed in claim 1, wherein the object is subjected to a respiratory movement and the recording of the two-dimensional projection image is controlled by a respiratory triggering.

13. The method as claimed in claim 1, wherein the object is subjected to a heart beat movement and the recording of the two-dimensional projection images is controlled by an ECG triggering.

14. The method as claimed in claim 1, wherein the position marker marks a position of a planned ablation during a procedure selected from the group consisting of: an electrophysiological intervention, a vessel path, a bile-duct containing a contrast agent, and a contour of a heart chamber.

15. A device for marking a three-dimensional structure on a two-dimensional projection image of an object recorded with an image recording system, comprising:

a first data storage device for storing two two-dimensional projection images of the object from two different projection directions;

a position determining device for determining a position marker on each of the two two-dimensional projection images;

a computer programmed to (i) calculate coordinates of the position marker on the each of the two two-dimensional projection images in a three-dimensional space and a theoretical position of the position marker on a further recorded two-dimensional projection image recorded from a further projection direction and (ii) generate an image with the position marker superimposed on the further recorded two-dimensional projection image in accord with the calculated theoretical position of the position marker;

a second data storage device for storing the further recorded two-dimensional projection image; and a screen for displaying the further recorded two-dimensional projection image with the position marker superimposed thereon.

16. The device as claimed in claim 15, wherein the image recording system is a part of an x-ray device and comprises an x-ray tube and an x-ray detector.

17. The device as claimed in claim 15, wherein the x-ray tube and the x-ray detector of the image recording system is movable about the object.

18. The device as claimed in claim 15, wherein the image recording system is a C-arm system and the x-ray tube and the x-ray detector are fixed to the C-arm which is rotated around the object.

19. The device as claimed in claim 15, wherein the object is a part of a human or animal body and the computer is programmed to determine a position marker on each of the two two-dimensional projection images by marking a structure which is only visible in the short term with use of a contrast means.

* * * * *